(12) United States Patent
Radolovich

(10) Patent No.: US 6,925,853 B2
(45) Date of Patent: Aug. 9, 2005

(54) AIR QUALITY SAMPLER USING SOLID PHASE COATED MATERIAL

(75) Inventor: Giuliano Radolovich, Leawood, KS (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 10/279,473

(22) Filed: Oct. 24, 2002

(65) Prior Publication Data

US 2004/0079137 A1 Apr. 29, 2004

(51) Int. Cl.⁷ .......................... G01N 19/10; G01N 7/00; G01N 30/96; G01N 1/18; G01F 1/32
(52) U.S. Cl. ...................... 73/31.03; 73/861.23; 422/88; 436/178
(58) Field of Search .......................... 73/24.03, 31.03, 73/863.21, 863.23; 422/88; 436/178

(56) References Cited

U.S. PATENT DOCUMENTS

| | | | | | |
|---|---|---|---|---|---|
| 4,102,201 | A | * | 7/1978 | Trine et al. | 73/863.21 |
| 4,942,135 | A | * | 7/1990 | Zaromb | 436/178 |
| 5,496,741 | A | * | 3/1996 | Pawliszyn | 436/163 |
| 5,498,549 | A | * | 3/1996 | Nagel et al. | 436/172 |
| 5,552,324 | A |   | 9/1996 | Liu | |
| 5,843,311 | A | * | 12/1998 | Richter et al. | 210/634 |
| 5,918,289 | A | * | 6/1999 | Scheppers et al. | 73/863.21 |
| 6,011,479 | A |   | 1/2000 | Morgan et al. | |
| 6,152,990 | A | * | 11/2000 | Allen et al. | 95/90 |
| 6,187,596 | B1 |   | 2/2001 | Dallas et al. | |
| 6,248,153 | B1 |   | 6/2001 | Braun et al. | |
| RE37,353 | E |   | 9/2001 | Kreikebaum et al. | |
| 2002/0172633 | A1 | * | 11/2002 | Koermer et al. | 423/219 |
| 2003/0115859 | A1 | * | 6/2003 | Deeba | 60/297 |

* cited by examiner

*Primary Examiner*—Michael Cygan
(74) *Attorney, Agent, or Firm*—Lathrop & Gage, L.C.

(57) ABSTRACT

A method and apparatus for monitoring air quality is provided.

20 Claims, No Drawings

AIR QUALITY SAMPLER USING SOLID PHASE COATED MATERIAL

FIELD OF THE INVENTION

This invention relates generally to a method and apparatus for monitoring air components.

BACKGROUND OF THE INVENTION

The composition and quality of ambient air in any given area may vary depending on a number of factors, including the presence of air pollution and various airborne contaminants. These contaminants may include biological materials, including bacteria and viruses, as well as chemical materials, such as pollutants and toxins.

In order to determine the air quality, the ambient air may be monitored. Monitoring may be effected in a variety of ways. Typically, samples of air are collected at specific locations for a given period of time, followed by the analysis of the samples using any number of known analytical techniques.

U.S. Pat. No. 6,011,479, issued Jan. 4, 2000, provides a personal continuous air monitor capable of sensing radiation. This air monitor employs a filter or detector head with a radiation detector and a series of signal processing units.

U.S. Pat. No. 6,187,596, issued Feb. 13, 2001, provides a visual airborne contaminant indicator employing a colored pH indicator, which may be used with an adsorptive filter.

U.S. Pat. No. 6,248,153, issued Jun. 19, 2001, provides a diffusional gas transfer system for removing airborne particles.

However, it would be a significant contribution to the art to provide an improved, versatile method and apparatus for monitoring air quality.

SUMMARY OF THE INVENTION

The present invention provides a method for monitoring air quality.

The invention further provides an apparatus for use in monitoring air quality.

DETAILED DESCRIPTION OF THE INVENTION

Collection of a sample of air to be monitored may be achieved by any number of means. In the present invention, air is contacted with a collection device employing a filter prepared from an adsorbent carbon-based resin.

The contacting process of the air with the filter during the collection process may be either active or passive. An air pump may be employed to actively draw air through the filter in order to collect a sample. Passive sample collection does not employ any additional physical or chemical means during the collection process other than the direct contact of the sampling device with the air to be monitored or sampled.

Adsorbable material is material that is capable of being adsorbed onto a surface during the collection process, and may include gaseous or particulate matter. Gaseous matter may include material that occurs normally in the gaseous state, or may include matter that has become volatilized. The term "normally" refers to the existing physical conditions, such as temperature and pressure. Particulate material includes matter that is not normally gaseous, as well as matter that has achieved an airborne state. This particulate material may further be delineated as biological or non-biological. Examples of biological material include both microscopic organisms, such as bacteria, such as anthrax bacilli, viruses, and fungi; spores, including fungal and bacterial spores, and pollen; and non-microscopic organisms, such as airborne insects. Examples of non-biological material include soot, particulate matter, airborne molecules, including both organic and inorganic molecules, and other chemical material.

During the collection process, material absorbed onto the surface of the sampler may also then diffuse into the sampling medium employed. Diffusion is the mechanism by which components of a mixture are transported around the mixture by means of random molecular or Brownian motion. The flow of mass by diffusion or flux across a plane is proportional to the concentration gradient of the diffusant across that plane. In general, transport of material through membranes may be further characterized by Fick's First and Second Laws of Diffusion. Fick's First Law states that the flux, J, of a component of concentration, C, across a membrane of unit area, in a predefined plane, is proportional to the concentration differential across that plane, and is expressed by the following equation: $J=-DVC$.

The sampler apparatus is generally prepared by applying an adsorbant material to a support suitably proportioned to the sampling device. Suitable adsorbent materials include carbon molecular sieves. A carbon molecular sieve is the carbon skeletal framework remaining after the pyrolysis of a polymeric precursor. These materials are primarily used for collecting very small molecular-sized compounds (for example, chloromethane, vinyl chloride, and Freon® compounds). The size and shape of the absorbed material, including analyte molecules, and the size and shape of the pores in the adsorbent particle determine how well the airborne material being monitored is adsorbed and desorbed. Suitable carbon molecular sieve materials include Carbosieve™ S-III and Carboxen™ carbon molecular sieves, available from Supelco. These carbon molecular sieve materials perform well at ambient temperature and pressure, and have upper temperature limits of at least 400° C. Carbosieve™ S-III has a large surface area (approximately 820 m2/g) and 15–40 Å pores, which makes the Carbosieve™ S-III spherical carbon molecular sieve excellent for trapping small airborne molecules, such as chloromethane. Although hydrophobic, Carbosieve™ S-III retains slightly more water during the sampling process than does Carboxen™-569. The pure carbon framework permits thermal desorption of the analyte molecules. Carboxen™ carbon molecular sieves are highly hydrophobic, thus providing accurate sampling at high humidities. Carboxen™ adsorbents also have higher capacity (or higher breakthrough volume) for many volatile organic compounds (VOCs). Carboxen™-1000 adsorbent has a large surface area and optimized microporosity, which enables it to effectively and efficiently adsorb and desorb smaller molecular size compounds, providing excellent chromatography without a need for cryogenic cooling.

Preferred for the practice of the present invention is an adsorbent mixture containing a carbon molecular sieve material as discussed above, along with polydimethylsiloxane, and a platinum catalyst. The preferred proportions of these materials are about 300–400 milligrams of carbon molecular sieve, about 300–400 milligrams of polydimethylsiloxane, and about 10–20 microliters of platinum catalyst. The most preferred proportions of these materials is 360 milligrams of carbon molecular sieve, 360 milligrams of polydimethylsiloxane, and 15 microliters of platinum catalyst. The preferred platinum catalyst is a platinum hydrosilylation catalyst available from Supelco.

This adsorbent material containing a carbon-based resin or material is typically coated onto a suitable substrate, which may include aluminum or any variety of metals or materials. A suitable substrate will withstand exposure to the conditions encountered during the preparation of the sampling apparatus, as well as conditions encountered during the sampling and sample collection process.

The adsorbent material that is coated onto the substrate is typically then cured to provide optimum performance during the sample collection process. The curing recipe is generally tailored for the substrate. Aluminum is the preferred substrate, although any substrate may be employed that can be coated with the adsorbent material chosen. Other types of substrates may require different curing parameters. Aluminum coated with a substrate is typically cured in a dry inert environment, typically employing helium or argon gas. Depending on the adsorbent material being coated on the aluminum, increased temperature may be used to hasten the curing process. Increased temperature may range from 250 to 300° C.

The size of the sampling device or filter is not critical, but is generally tailored to fit the overall size of the air collection device so as to provide optimum sample recovery. Preferred for the practice of the present invention is a filter diameter between about 0.2 cm to about 5 cm. The most preferred overall dimensions of the collection device of the instant invention is 1.6 cm by 2.0 cm.

Prior to the sampling process and in order to ensure accurate sampling, the device is kept in a contaminant-free environment.

The present invention can be mounted to any surface or structure by any permanent or non-permanent means.

As discussed above, the sampling process may be either active or passive. The sampling time may be for any suitable time that would sample or collect a sufficient amount of material that can be detected and analyzed.

The sample containing the possible airborne contaminants may be desorbed or extracted from the adsorbant or filter by any suitable physical or chemical means for analysis. Typically, the sample is chemically extracted from the filter by using a suitable solvent or solvent system. Suitable solvents include organic solvents, such as acetone, methanol, ethanol, methylene chloride, or $CS_2$, or inorganic solvents, such as water. High purity solvents are recommended (for example, low benzene $CS_2$) for desorbing the collected materials. Solvent systems may employ a mixture of more than one solvent to achieve optimal sample desorption. The solvent selected will be suitable for the extraction of the sample from the specific collection device, and will be selected based on the particular elements of said collection device. Specifically, a different solvent may be employed with an aluminum based collection device than with a collection device based on another type of metal. One skilled in the art will be capable of selecting the optimum solvent or solvent system. The solvent is additionally further analyzed for impurities as a control. A preferred solvent for the practice of the present invention is methylene chloride.

In order to provide an accurate reading, during the desorption process the integrity of the samples must be maintained, and the samples must not be exposed to any contaminants. The desorbed material is then analyzed using chromatography, gravimetry, titration, potentiometric analysis, coulometric analysis, spectrophotometric analysis, or any other suitable analytical means. The preferred analytical means for the practice of the present invention is gas chromatography.

The present invention provides a high amount of surface area compared to the total mass of collection media utilized for passive sampling of chemicals from the ambient air. Preferred for the practice of the present invention is a ratio of about 1–4 mg of collection media per square centimeter of surface area.

The benefits of this design include an uptake rate, or pumping rate, that exceeds 100 mls per minute, as well as complete or efficient recovery of the sample by simple sonication, with negligible chemical artifacts due to the thin surface coating.

EXAMPLES

Abbreviations, Matrials, and Sources of Materials:

Carboxen™ is a carbon-based molecular sieve adsorbent resin commercially available from Supelco (a licensed product of Rohm and Haas).

Example 1

Preparation of Sampling Device

A piece of thin aluminum foil was cut to size, and both sides were prepared by polishing with 600 grit polishing paper and then oxidized at 280° C. for 2 hours.

Both sides of the foil were coated with a prepared slurry of Carboxen™ (available from Supelco), polydimethylsiloxane (available from Supelco) and a platinum hydrosilylation catalyst (available from Supelco).

Specifically, 360–365 mg of polydimethylsiloxane was dissolved in 10 ml of dichloromethane. Dissolution of the PDMS requires a minumum of 3–4 hours without agitation. Allowing the PDMS to dissolve over night is preferred. The PDMS solution was transferred to a vial containing 360–365 mg of carbon molecular sieve, using an additional 10 ml of dichloromethane. The mixture was then shaken vigorously. Using an ultrasonic probe, the mixture was sonicated for about 1 minute at 5 Watts input power. 15 µl of the platinum catalyst was then added, and the mixture was again shaken vigorously. For best results, the coating mixture was applied within 2 hours of preparation.

The coating was then applied with a pneumatic spray applicator. The desirable coating thickness is not critical, but should be greater than 25 microns. (Thicknesses beyond 100 microns do not enhance sampler performance, and are not necessary.) When coating was completed, the coated foil was conditioned by heating at 280° C. for two hours in the presence of nitrogen or another inert gas.

The coated foil was then stored in a clean container until needed or until used in the sampling device.

Example 2

Sampling Process

The sampler is operated by removing from the protective container and placed in contact with the air at a location of interest. The sampling duration time is variable, and may range from just a few minutes to a few weeks.

Example 3

Analysis of Collected Sample

After the sampling period, the sampler is stored in a clean container until ready for analysis. Analysis begins with the removal of the sampler from the container and placement into a clean vial. Analysis grade acetone or methylene chloride or another suitable organic solvent is added to cover the sampler's entire coated surface and the vial is sealed and sonicated for at least 30 seconds. Methylene chloride is preferred. The acetone serves to extract the adsorbed chemicals from the coated sampler. A portion of the acetone may be analyzed directly by gas chromatography or alternate analytical means. The acetone extract may be optionally concentrated prior to analysis in order to improve sensitivity by way of a rotovap or other suitable device.

Example 4

Control or Baseline

The effectiveness of the sampler is verified by exposure to known chemical vapor concentrations for a fixed sampling time followed by analysis. The passive sampler is considered semi-quantitative in terms of providing vapor concentration from sampled air. However, under well-controlled conditions, the passive sampler is also able to produce accurate chemical concentrations

I claim:

1. A method for monitoring air quality which comprises:
   (a) contacting a collection device comprising a carbon-based adsorbent resin which additionally comprises polydimethylsiloxane and a platinum catalyst with air;
   (b) collecting a sample from said air over a period of time from about 24 hours to about one week using said collection device;
   (c) removing adsorbed material from said collection device; and
   (d) analyzing said removed material.

2. The method of claim 1 wherein said adsorbed material is removed from said collection device by physical means.

3. The method of claim 2 wherein said physical means is selected from the group consisting of sonication, a change in temperature, and a change in pressure.

4. The method of claim 1 wherein said adsorbed material is removed from said collection device by chemical means.

5. The method of claim 4 wherein said chemical means is solvent extraction.

6. The method of claim 5 wherein said solvent is selected from the group consisting of acetone, methanol, ethanol, methylene chloride, $CS_2$, and water.

7. The method of claim 6 wherein said solvent is acetone.

8. The method of claim 6 wherein said solvent is methanol.

9. The method of claim 6 wherein said solvent is ethanol.

10. The method of claim 6 wherein said solvent is methylene chloride.

11. The method of claim 6 wherein said solvent is $CS_2$.

12. The method of claim 6 wherein said solvent is water.

13. The method of claim 1 wherein said collected sample is chemical material.

14. The method of claim 13 wherein said chemical material is soot.

15. An apparatus for monitoring air quality which comprises a collection device comprising an adsorbent material, wherein said adsorbent material is a carbon molecular sieve which additionally comprises polydimethylsiloxane and a platinum catalyst.

16. The apparatus of claim 15 wherein said carbon molecular sieve material has a high surface area.

17. The apparatus of claim 15 wherein said surface area is from about 10 $cm^2$ to about 20 $cm^2$.

18. The apparatus of claim 15 wherein said collection device is selected from the group consisting of an active collection device and a passive collection device.

19. The apparatus of claim 18 wherein said collection device is an active collection device.

20. The apparatus of claim 18 wherein said collection device is a passive collection device.

* * * * *